(12) United States Patent
Tanaka et al.

(10) Patent No.: US 12,408,840 B2
(45) Date of Patent: Sep. 9, 2025

(54) COMPONENT CONCENTRATION MEASURING DEVICE

(71) Applicant: Nippon Telegraph and Telephone Corporation, Tokyo (JP)

(72) Inventors: Yujiro Tanaka, Tokyo (JP); Masahito Nakamura, Tokyo (JP); Daichi Matsunaga, Tokyo (JP); Michiko Seyama, Tokyo (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 916 days.

(21) Appl. No.: 17/417,556

(22) PCT Filed: Dec. 11, 2019

(86) PCT No.: PCT/JP2019/048420
§ 371 (c)(1),
(2) Date: Jun. 23, 2021

(87) PCT Pub. No.: WO2020/137537
PCT Pub. Date: Jul. 2, 2020

(65) Prior Publication Data
US 2022/0054016 A1    Feb. 24, 2022

(30) Foreign Application Priority Data
Dec. 25, 2018    (JP) ................... 2018-240802

(51) Int. Cl.
*A61B 5/00*    (2006.01)
*A61B 5/145*    (2006.01)

(52) U.S. Cl.
CPC ........ *A61B 5/0095* (2013.01); *A61B 5/14532* (2013.01)

(58) Field of Classification Search
CPC .......................... A61B 5/0095; A61B 5/14532
See application file for complete search history.

(56) References Cited

U.S. PATENT DOCUMENTS

| | | | |
|---|---|---|---|
| 2013/0123590 A1* | 5/2013 | Naganuma | A61B 5/6826 600/316 |
| 2019/0014989 A1* | 1/2019 | Tanaka | A61B 5/0095 |

FOREIGN PATENT DOCUMENTS

JP    2010104858 A    5/2010

* cited by examiner

*Primary Examiner* — Daniel L Cerioni
(74) *Attorney, Agent, or Firm* — Slater Matsil, LLP

(57) ABSTRACT

A light emitting unit irradiates a measurement site of a measurement subject with a light beam having a wavelength that is absorbed by a measurement target substance. A detection unit detects a photoacoustic signal generated in the measurement site irradiated with the light beam emitted from the light emitting unit. A resonator is arranged so as to clamp the measurement site, and causes the above-described photoacoustic signal to resonate. The resonator is constituted by a first reflection unit and a second reflection unit. The first reflection unit is arranged between the light irradiation unit and the measurement site. Also, the light beam passes through the first reflection unit. The second reflection unit is arranged between the detection unit and the measurement site.

6 Claims, 5 Drawing Sheets

COMPONENT CONCENTRATION MEASURING DEVICE

CROSS-REFERENCE TO RELATED APPLICATIONS

This application is a national phase entry of PCT Application No. PCT/JP2019/048420, filed on Dec. 11, 2019, which claims priority to Japanese Application No. 2018-240802, filed on Dec. 25, 2018, which applications are hereby incorporated herein by reference.

TECHNICAL FIELD

The present invention relates to a component concentration measuring device, and more specifically relates to a component concentration measuring device for non-invasively measuring the concentration of a component such as glucose in blood.

BACKGROUND

Knowing (measuring) the blood glucose level is very important when determining an insulin dosage for a person with diabetes, preventing diabetes, and so on. The blood glucose level is the concentration of glucose in blood, and photoacoustics is a well-known method for measuring the concentration of this type of component (see PTL 1).

When a living body is irradiated with a certain amount of light (electromagnetic waves), the emitted light is absorbed by molecules of the living body. For this reason, measurement target molecules in the portion irradiated with light are locally heated and expand, thus emitting acoustic waves. The pressure of such acoustic waves is dependent on the quantity of molecules that absorb the light. Photoacoustics is a method of measuring a molecular quantity in a living body by measuring such acoustic waves. Acoustic waves are pressure waves that propagate in a living body and have a characteristic of undergoing less diffusion than electromagnetic waves, and therefore photoacoustics can be said to be suited to the measurement of a blood component in a living body.

Photoacoustic measurement makes it possible to continuously monitor the glucose concentration in blood. Furthermore, photoacoustic measurement does not require a blood sample, and does not cause the measurement subject discomfort.

CITATION LIST

Patent Literature

PTL 1 Japanese Patent Application Publication No. 2010-104858

SUMMARY

Technical Problem

Meanwhile, in this type of measurement, when performing continuous measurement without imposing a significant burden on the measurement subject, a person's ear lobe is used as a measurement site, and it is important to attach a compact device to the measurement site. Low power consumption is essential to obtain a compact device, and thus the intensity of light to be emitted cannot be increased. In such a state in which the light intensity cannot be increased, acoustic waves (photoacoustic signal) that are obtained are so small that it cannot be measured with high sensitivity. As a result, there is the problem that the accuracy of the measurement deteriorates.

Embodiments of the present invention were achieved in order to solve the foregoing problems, and an object of embodiments of the present invention is to make it possible to measure the concentration of a component in a human body using photoacoustics more accurately.

Means for Solving the Problem

A component concentration measuring device according to embodiments of the present invention includes: a light emitting unit configured to irradiate a measurement site of a measurement subject with a light beam having a wavelength that is absorbed by a measurement target substance; a detection unit configured to detect a photoacoustic signal generated in the measurement site irradiated with the light beam; and a resonator that is arranged so as to clamp the measurement site, and is configured to cause the photoacoustic signal to resonate, wherein the resonator includes: a first reflection unit that is arranged between the light emitting unit and the measurement site and has a first reflection surface configured to reflect the acoustic signal while allowing the light beam to pass; and a second reflection unit that is arranged between the detection unit and the measurement site and has a second reflection surface configured to reflect the photoacoustic signal.

In a configuration example of the component concentration measuring device, the first reflection surface and the second reflection surface are parallel to each other.

In a configuration example of the component concentration measuring device, an acoustic matching unit configured to fill up a gap between the second reflection unit and the measurement site is further included.

In a configuration example of the component concentration measuring device, the first reflection surface faces the measurement site, and the first reflection unit includes: a first contact surface that faces the light emitting unit and is in contact with a light emitting end of the light emitting unit; and a void formed between the first reflection surface and the first contact surface.

In a configuration example of the component concentration measuring device, the second reflection surface faces the measurement site, and the second reflection unit includes: a second contact surface that faces the detection unit and is in contact with a detection face of the detection unit that faces the measurement site; and a void formed between the second reflection surface and the second contact surface.

In a configuration example of the component concentration measuring device, a concentration calculation unit configured to obtain a concentration of the substance based on the photoacoustic signal is further included.

In a configuration example of the component concentration measuring device, the substance is glucose, and the light emitting unit emits the light beam having a wavelength that is absorbed by glucose.

Effects of Embodiments of the Invention

As described above, according to embodiments of the present invention, since the resonator is arranged so as to clamp a measurement site, an excellent effect can be achieved that it is possible to measure the concentration of a component in a human body using photoacoustics more accurately.

DETAILED DESCRIPTION OF ILLUSTRATIVE EMBODIMENTS

Figure 1:
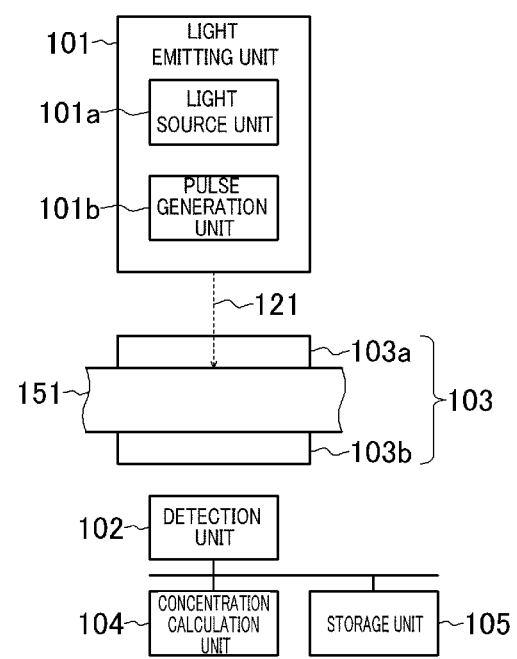
FIG. 1 is a configuration diagram illustrating a configuration of a component concentration measuring device according to an embodiment of the present invention.

The following describes a component concentration measuring device according to an embodiment of the present invention, with reference to FIG. 1. The component concentration measuring device includes a light emitting unit 101, a detection unit 102, a resonator 103, a concentration calculation unit 104, and a storage unit 105.

The light emitting unit 101 generates a light beam 121 having a wavelength that is absorbed by a measurement target substance, and emits the generated light beam 121 toward a measurement site 151. For example, in the case where the measurement target substance is glucose in blood, the light emitting unit 101 includes a light source unit 101a that generates the light beam 121 having a wavelength that is absorbed by glucose, and a pulse generation unit 101b that converts the light beam 121 generated by the light source into pulsed light that has a pre-set pulse width.

Note that glucose exhibits a property of absorbing light in wavelength bands near 1.6 μm and 2.1 μm (see PTL 1). The above-described pulsed light beam 121 is obtained by the pulse generation unit 101b. If glucose is the measurement target substance, the light emitting unit 101 (pulse generation unit 101b) emits the light beam 121 having a pulse width of 0.02 seconds or longer.

The detection unit 102 detects a photoacoustic signal generated in the measurement site 151 that was irradiated with the light beam emitted by the light emitting unit 101. The detection unit 102 can be a unit that employs a piezoelectric effect or an electrostrictive effect (e.g., a crystal microphone, a ceramic microphone, or a ceramic ultrasonic sensor), a unit that employs electromagnetic induction (e.g., a dynamic microphone or a ribbon microphone), a unit that employs an electrostatic effect (e.g., a condenser microphone), or a unit that employs magnetostriction (e.g., a magnetostrictive vibrator). For example, in the case of employing a piezoelectric effect, the unit includes a crystal made of a frequency flat-type electrostrictive element (ZT) or PVDF (polyvinylidene fluoride). The detection unit 102 can also be constituted by a PZT that includes an FET (Field Effect Transistor) amplifier. The photoacoustic signal detected by the detection unit 102 is stored in the storage unit 105 together with information regarding the time at which the signal was measured, for example.

Figure 2:
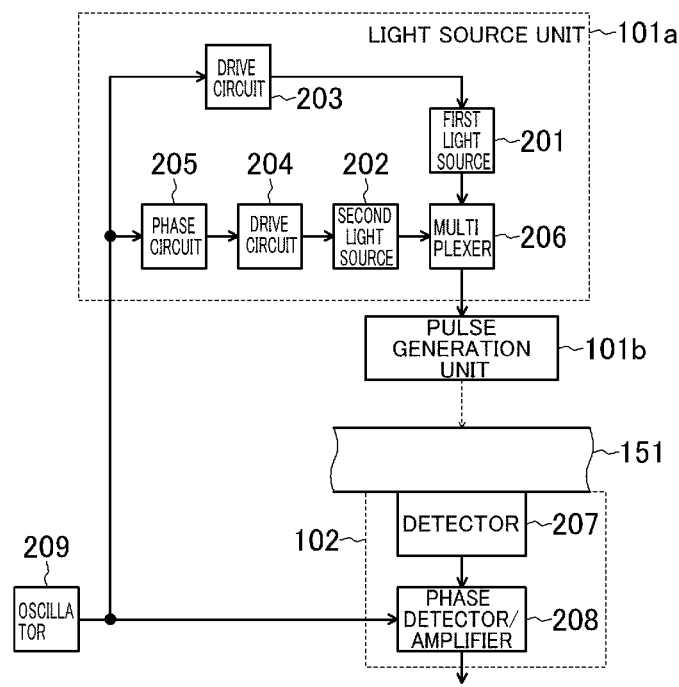
FIG. 2 is a configuration diagram illustrating in more detail the configuration of the component concentration measuring device according to the embodiment of the present invention.

The following is a more detailed description of the light emitting unit 101 and the detection unit 102 with reference to FIG. 2. First, the light source unit 101a includes a first light source 201, a second light source 202, a drive circuit 203, a drive circuit 204, a phase circuit 205, and a multiplexer 206. Also, the detection unit 102 includes a detector 207, a phase detector/amplifier 208, and an oscillator 209.

The oscillator 209 is connected to the drive circuit 203, the phase circuit 205, and the phase detector/amplifier 208 via signal lines. The oscillator 209 transmits signals to the drive circuit 203, the phase circuit 205, and the phase detector/amplifier 208.

The drive circuit 203 receives the signal transmitted from the oscillator 209, and supplies a drive voltage to the first light source 201 so as to cause the first light source 201 to emit light whose intensity has been modulated in synchronization with the frequency of the signal. The first light source 201 is, for example, a semiconductor laser.

The phase circuit 205 receives the signal transmitted from the oscillator 209, changes the phase of the received signal by 180 degrees, and transmits the resultant signal to the drive circuit 204 via a signal line.

The drive circuit 204 receives the signal transmitted from the phase circuit 205, and supplies a drive voltage to the second light source 202 so as to cause the second light source 202 to emit light whose intensity has been modulated at the frequency of the above-described signal and in synchronization with the signal subjected to the phase change of 180 degrees by the phase circuit 205. The second light source 202 is, for example, a semiconductor laser.

The first light source 201 and the second light source 202 respectively output light beams that have mutually different wavelengths, and the light beams output by the light sources are each guided to the multiplexer 206 by an optical wave transmitting means. The wavelengths of the first light source 201 and the second light source 202 are set such that the wavelength of one of the light beams is a wavelength absorbed by glucose, and the wavelength of the other light beam is a wavelength absorbed by water. Also, the wavelengths of the light sources are set so that the degrees of absorption of the light beams are equal to each other.

The light beam output by the first light source 201 and the light beam output by the second light source 202 are multiplexed into a single light beam in the multiplexer 206, and the single light beam is then incident on the pulse generation unit 101b. Upon receiving the light beam, the pulse generation unit 101b converts the incident light beam into pulsed light that has a predetermined pulse width, and emits the pulsed light to the measurement site 151. In the measurement site 151 irradiated with the pulsed light beam in this way, a photoacoustic signal is internally generated.

The detector 207 detects the photoacoustic signal generated in the measurement site 151, converts the detected photoacoustic signal into an electric signal, and transmits the electric signal to the phase detector/amplifier 208 via a signal line. The phase detector/amplifier 208 receives a synchronization signal that is necessary for synchronous detection and was transmitted from the oscillator 209, and receives the electric signal that is proportional to the photoacoustic signal and was transmitted from the detector 207, performs synchronous detection, amplification, and wave filtering, and outputs the resultant electric signal that is proportional to the photoacoustic signal. The electric signal (photoacoustic signal) that was measured and processed in this way is stored in the storage unit 105 together with information regarding the time at which the signal was measured.

The intensity of the signal output from the phase detector/amplifier 208 is proportional to the amounts of light that were absorbed by components (glucose and water) in the measurement site 151 and respectively output by the first light source 201 and the second light source 202, and thus the intensity of the signal is proportional to the amounts of such components in the measurement site 151. The concentration calculation unit 104 obtains, based on the measured value of the intensity of the signal (photoacoustic signal) output in this way, the component amount (concentration) of the measurement target substance (glucose) in blood within the measurement site 151.

As described above, two beams of light that have been subjected to intensity modulation based on signals having the same frequency are used in order to eliminate the influence of the non-uniformity of frequency characteristics when using a plurality of light beams, which is problematic when intensity modulation is performed based on signals having a plurality of frequencies.

On the other hand, nonlinear absorption coefficient dependence of a photoacoustic signal, which is problematic in measurement using photoacoustics, can be resolved by performing the measurement using light beams that have different wavelengths but have the same absorption coefficient as described above (see PTL 1).

The resonator 103 is arranged while clamping the measurement site 151, and causes the above-described photoacoustic signal to resonate. The resonator 103 is constituted by a first reflection unit 103a and a second reflection unit 103b. The first reflection unit 103a is arranged between the light irradiation unit 101 and the measurement site 151. Also, a light beam passes through the first reflection unit 103a. The second reflection unit 103b is arranged between the detection unit 102 and the measurement site 151.

Figure 3:
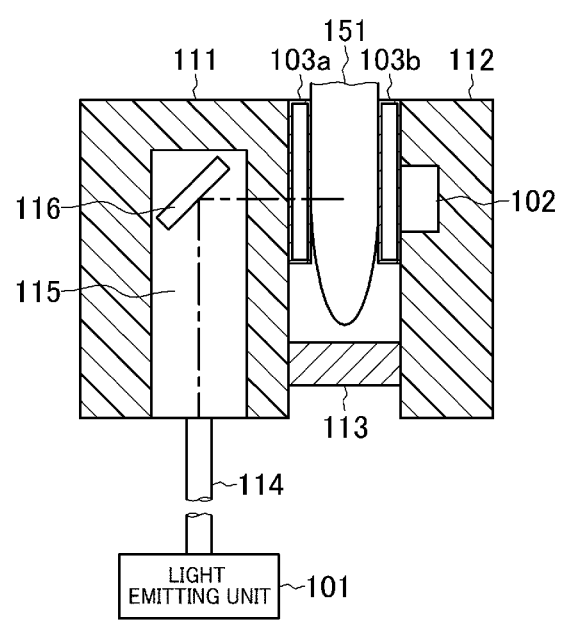
FIG. 3 is a cross-sectional view illustrating a portion of the configuration of the component concentration measuring device according to the embodiment of the present invention.

As shown in FIG. 3 for example, the component concentration measuring device includes a pair of first holding member 111 and second holding member 112 that are capable of clamping and holding the measurement site 151. The measurement site 151 is an ear lobe, for example. The first holding member 111 and the second holding member 112 are coupled to each other by a coupling portion 113. A coil spring (not shown) that biases the first holding member 111 and the second holding member 112 in a closing direction is fitted around the coupling portion 113. The measurement site 151 is sandwiched between the first holding member 111 and the second holding member 112 due to the closing direction force applied by the coil spring.

The light beam emitted from the light emitting unit 101 is introduced into the first holding member 111 by an optical fiber 114. The introduced light beam passes through an optical system 115 provided inside the first holding member 111, and is then reflected by a reflection unit 116. In a state in which the measurement site 151 is sandwiched between the first holding member 111 and the second holding member 112, the light beam reflected by the reflection unit 116 is incident on the measurement site 151.

The second holding member 112 includes the detection unit 102. The detection unit 102 detects a photoacoustic signal generated in the measurement site 151 as a result of the light beam being incident on the measurement site 151 in the state in which the measurement site 151 is sandwiched between the first holding member 111 and the second holding member 112.

In the embodiment, the first reflection unit 103a is arranged between the first holding member 111 and the measurement site 151, and the second reflection unit 103b is arranged between the second holding member 112 and the measurement site 151. The first reflection unit 103a is pressed against the measurement site 151 by the first holding member 111. The second reflection unit 103b is pressed against the measurement site 151 by the second holding member 112.

Figure 4:
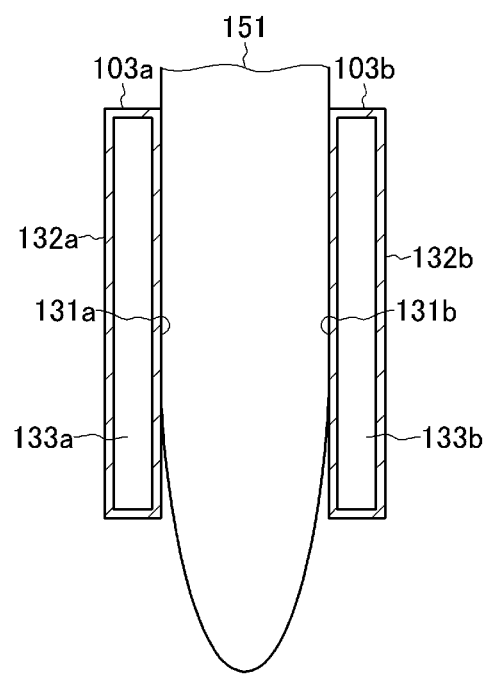
FIG. 4 is a cross-sectional view illustrating a portion of the configuration of the component concentration measuring device according to the embodiment of the present invention.

As shown in FIG. 4, the first reflection unit 103a includes a first reflection surface 131a that faces the measurement site 151, and is configured to reflect the photoacoustic signal. The first reflection surface 131a is arranged so as to be in contact with the measurement site 151. Also, the second reflection unit 103b includes a second reflection surface 131b that faces the measurement site 151, and is configured to reflect a photoacoustic signal. The second reflection surface 131b is arranged so as to be in contact with the measurement site 151. The first reflection surface 131a and the second reflection surface 131b are parallel to each other.

On the other hand, the first reflection unit 103a includes a first contact surface 132a that faces the light emitting unit 101. A portion of the first holding member 111 that serves as a light emitting end of the light emitting unit 101 is in contact with the first contact surface 132a. Also, the second reflection unit 103b includes a second contact surface 132b that faces the detection unit 102. A detection face of the detection unit 102 is in contact with the second contact surface 132b. Also, in this example, a void 133a is formed between the first reflection surface 131a and the first contact surface 132a. Similarly, a void 133b is formed between the second reflection surface 131b and the second contact surface 132b.

As described above, a photoacoustic signal is generated as a result of the light beam reflected by the reflection unit 116 being incident on the measurement site 151 sandwiched between the first reflection unit 103a and the second reflection unit 103b, and the photoacoustic signal is reflected between the first reflection surface 131a and the second reflection surface 131b. If the first reflection surface 131a and the second reflection surface 131b are separated at a distance at which the generated photoacoustic signal resonates (vibrates sympathetically), the photoacoustic signal resonates due to the resonator 103 constituted by the first reflection unit 103a and the second reflection unit 103b, and a larger acoustic pressure can be obtained. As a result, even when the concentration of the target component is the same, the signal detected by the detection unit 102 is larger than in a case when the resonator 103 is not included, and thus an improvement in sensitivity is expected.

Note that since the void 133a is provided between the first reflection surface 131a and the first contact surface 132a, which is in contact with the portion of the first holding member 111 that serves as the light emitting end of the light emitting unit 101, it is possible to suppress a reduction in the reflectance of the photoacoustic signal at the first reflection surface 131a.

Similarly, since the void 133b is provided between the second reflection surface 131b and the second contact surface 132b, which is in contact with the detection face of the detection unit 102, it is possible to suppress a reduction in the reflectance of the photoacoustic signal at the second reflection surface 131b.

Note that in the description above, a reduction in the reflectance of the photoacoustic signal at the first reflection surface 131a and the second reflection surface 131b is suppressed by providing the voids 133a and 133b as cuboid spaces, but the present invention is not limited to this. The first reflection unit 103*a* and the second reflection unit 1*o*3*b* may be made of a porous body such as a sonic crystal, and the voids may be constituted by the porous bodies.

As described above, according to embodiments of the present invention, since the resonator can increase the acoustic pressure of a photoacoustic signal, the photoacoustic signal can be detected with higher sensitivity, and thus it is possible to measure the concentration of a component in a human body using photoacoustics more accurately.

Meanwhile, if glucose is the measurement target substance, the wavelength of an obtained photoacoustic signal is 250 to 350 Hz, and in this case, the distance between the two resonating reflection units (reflection faces) is about 5 mm. On the other hand, if the measurement site is an ear lobe for example, the thickness of the ear lobe may be less than 5 mm.

Figure 5:
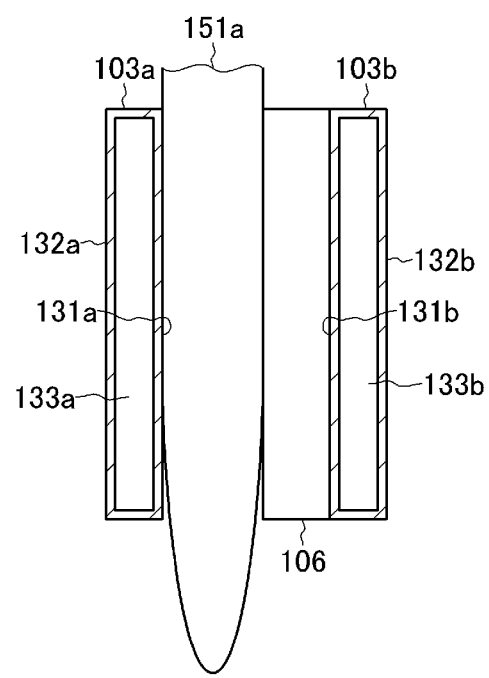
FIG. 5 is a cross-sectional view illustrating a portion of the configuration of the component concentration measuring device according to the embodiment of the present invention.

In such a case, as shown in FIG. 5, an acoustic matching unit 106 is arranged between a measurement site 151*a* and the second reflection unit 103*b*. The acoustic matching unit 106 is provided while filling up the gap between the second reflection unit 103*b* and the measurement site 151. The acoustic matching unit 106 is provided so as to be in contact with the measurement site 151*a*. Accordingly, in order to suppress a photoacoustic signal from reflecting between the measurement site 151*a* and the acoustic matching unit 106, the acoustic matching unit 106 is made of a material that has a predetermined acoustic impedance so that acoustic matching can be achieved therebetween.

As described above, according to embodiments of the present invention, since the resonator is arranged so as to clamp the measurement site, it is possible to measure the concentration of a component in a human body using photoacoustics more accurately.

Note that the present invention is not limited to the above-described embodiment, and it is apparent that various modifications and combinations can be implemented by a person skilled in the art to which the present invention pertains without departing from the technical idea of the present invention.

REFERENCE SIGNS LIST

101 Light emitting unit
101*a* Light source unit
101*b* Pulse generation unit
102 Detection unit
103 Resonator
103*a* First reflection unit
103*b* Second reflection unit
104 Concentration calculation unit
105 Storage unit.

The invention claimed is:

1. A component concentration measuring device comprising:

a light emitting device configured to irradiate a measurement site of a measurement subject with a light beam having a wavelength that is absorbed by a measurement target substance;
a detector configured to detect a photoacoustic signal generated in the measurement site irradiated with the light beam; and
a resonator that is arranged with the measurement site in between, and is configured to cause the photoacoustic signal to resonate, wherein the resonator includes:
a first reflector between the light emitting device and the measurement site and has a first reflection surface configured to reflect the photoacoustic signal while allowing the light beam to pass;
a second reflector between the detector and the measurement site and has a second reflection surface configured to reflect the photoacoustic signal, wherein the first reflection surface and the second reflection surface are parallel to each other; and
a gap between the first reflection surface and the second reflection surface is a gap at which the photoacoustic signal resonates.

2. The component concentration measuring device according to claim 1, further comprising:
a material filling a gap between the second reflector and the measurement site, wherein the material has a predetermined acoustic impedance.

3. The component concentration measuring device according to claim 1, wherein:
the first reflection surface faces the measurement site; and
the first reflector includes:
a first contact surface that faces the light emitting device and is in contact with a light emitting end of the light emitting device; and
a void between the first reflection surface and the first contact surface.

4. The component concentration measuring device according to claim 1, wherein:
the second reflection surface faces the measurement site; and
the second reflector includes:
a second contact surface that faces the detector and is in contact with a detection face of the detector that faces the measurement site; and
a void between the second reflection surface and the second contact surface.

5. The component concentration measuring device according to claim 1, wherein a concentration of the measurement target substance is obtained based on the photoacoustic signal.

6. The component concentration measuring device according to claim 1, wherein
the measurement target substance is glucose, and
the light emitting device is configured to emit the light beam having a wavelength that is absorbed by glucose.

* * * * *